(12) United States Patent
Kumar et al.

(10) Patent No.: US 8,469,279 B2
(45) Date of Patent: Jun. 25, 2013

(54) NETWORK AND METHOD FOR DATA INPUT, STORAGE AND RETRIEVAL

(75) Inventors: Arjun Prakash Kumar, Whitty (CA); Wai-Cheong Daniel Sin, Mississauga (CA)

(73) Assignee: SPQKumar Inc., Whitby (CA)

( * ) Notice: Subject to any disclaimer, the term of this patent is extended or adjusted under 35 U.S.C. 154(b) by 206 days.

(21) Appl. No.: 12/839,021

(22) Filed: Jul. 19, 2010

(65) Prior Publication Data
US 2011/0184994 A1    Jul. 28, 2011

(30) Foreign Application Priority Data
Jan. 22, 2010   (CA) ..................................... 2690784

(51) Int. Cl.
*G06K 19/05* (2006.01)

(52) U.S. Cl.
USPC .......................................... 235/492; 235/380

(58) Field of Classification Search
USPC ......................................... 235/492, 487, 380
See application file for complete search history.

(56) References Cited

U.S. PATENT DOCUMENTS

| | | | |
|---|---|---|---|
| 5,404,292 A | 4/1995 | Hendrickson |
| 5,494,292 A | 2/1996 | Mileti |
| 5,499,293 A | 3/1996 | Behram et al. |
| 5,763,862 A | 6/1998 | Jachimowicz |
| 5,778,882 A | 7/1998 | Raymond et al. |
| 5,832,488 A | 11/1998 | Eberhardt |
| 5,924,074 A | 7/1999 | Evans |
| 5,926,526 A | 7/1999 | Rapaport et al. |
| 5,970,463 A | 10/1999 | Cave et al. |
| 5,974,124 A | 10/1999 | Schlueter, Jr. et al. |
| 5,997,476 A | 12/1999 | Brown |
| 6,000,828 A | 12/1999 | Leet |
| 6,032,119 A | 2/2000 | Brown et al. |
| 6,044,349 A | 3/2000 | Tolopka |
| 6,073,106 A | 6/2000 | Rozen et al. |
| 6,082,776 A | 7/2000 | Feinberg |
| 6,088,677 A | 7/2000 | Spurgeon |
| 6,223,559 B1 | 5/2001 | Coleman |
| 6,457,647 B1 | 10/2002 | Kurihashi |
| 6,463,417 B1 | 10/2002 | Schoenberg |
| 6,574,484 B1 | 6/2003 | Carley |
| 6,725,200 B1 | 4/2004 | Rost |
| 6,738,784 B1 | 5/2004 | Howes |

(Continued)

FOREIGN PATENT DOCUMENTS

WO    03073353  A2    9/2003

OTHER PUBLICATIONS http://www.diytrade.com/china/4/products/5033095/usb_credit_card.html.

(Continued)

*Primary Examiner* — Daniel St.Cyr
(74) *Attorney, Agent, or Firm* — Bereskin and Parr LLP/S.E.N.C.R.L., s.r.l.

(57) ABSTRACT

A personal electronic carrier device (PECD) comprising means for receiving PECD data; means for storing PECD data; means for transmitting PECD data directly or indirectly PECD; and operating software means to effect the receiving, storing and transmitting the PECD data. The PECD is part of a network having a plurality of data stations and preferably a main data base. The PECD data is selected from the group consisting of medical, educational and identification data. The networks provide for the efficacious and convenient handling of data.

18 Claims, 6 Drawing Sheets

U.S. PATENT DOCUMENTS

| | | | |
|---|---|---|---|
| 6,766,952 B2 | 7/2004 | Luu | |
| 6,845,448 B1 | 1/2005 | Chaganti et al. | |
| 6,871,214 B2 | 3/2005 | Parsons et al. | |
| 6,941,271 B1 | 9/2005 | Soong | |
| 6,988,075 B1 | 1/2006 | Hacker | |
| 7,146,159 B1 | 12/2006 | Zhu | |
| 7,206,847 B1 | 4/2007 | Alberth | |
| 7,213,766 B2 * | 5/2007 | Ryan et al. | 235/492 |
| 7,257,967 B2 | 8/2007 | Rheinstein | |
| 7,303,120 B2 * | 12/2007 | Beenau et al. | 235/380 |
| 7,306,560 B2 | 12/2007 | Iliff | |
| 7,334,735 B1 | 2/2008 | Antebi | |
| 7,360,688 B1 | 4/2008 | Harris | |
| 7,395,215 B2 | 7/2008 | Grushka | |
| 7,472,833 B2 | 1/2009 | Justin | |
| 7,487,908 B1 | 2/2009 | Cook | |
| 7,494,058 B2 * | 2/2009 | Bonalle et al. | 235/380 |
| 7,578,437 B2 | 8/2009 | Lu | |
| 7,621,458 B2 | 11/2009 | Zellner | |
| 7,677,459 B2 | 3/2010 | Arnouse | |
| 7,721,109 B1 | 5/2010 | Herder | |
| 7,753,266 B2 | 7/2010 | Harris | |
| 8,180,654 B2 | 5/2012 | Berkman et al. | |
| 2001/0041991 A1 | 11/2001 | Segal et al. | |
| 2002/0046061 A1 | 4/2002 | Wright et al. | |
| 2002/0059587 A1 | 5/2002 | Cofano et al. | |
| 2002/0077861 A1 | 6/2002 | Hogan | |
| 2002/0103675 A1 | 8/2002 | Vanelli | |
| 2002/0116330 A1 | 8/2002 | Hed | |
| 2002/0120470 A1 | 8/2002 | Trice, Sr. | |
| 2002/0128865 A1 | 9/2002 | Alten | |
| 2002/0178631 A1 | 12/2002 | Morton | |
| 2002/0189146 A1 | 12/2002 | Lyon | |
| 2003/0014282 A1 | 1/2003 | Haaksma et al. | |
| 2003/0037065 A1 | 2/2003 | Svab | |
| 2003/0040940 A1 | 2/2003 | Nehammer | |
| 2003/0059751 A1 | 3/2003 | Welles | |
| 2003/0086591 A1 | 5/2003 | Simon | |
| 2003/0098356 A1 | 5/2003 | Gombar | |
| 2003/0132132 A1 | 7/2003 | Small | |
| 2003/0140044 A1 | 7/2003 | Mok et al. | |
| 2003/0208382 A1 | 11/2003 | Westfall | |
| 2003/0226889 A1 | 12/2003 | Morrison, Jr. | |
| 2003/0229452 A1 | 12/2003 | Lewis et al. | |
| 2003/0233844 A1 | 12/2003 | Rheinstein | |
| 2004/0078229 A1 | 4/2004 | Gay et al. | |
| 2004/0162895 A1 | 8/2004 | Mok et al. | |
| 2004/0186746 A1 | 9/2004 | Angst et al. | |
| 2004/0228336 A1 | 11/2004 | Kung et al. | |
| 2004/0232219 A1 | 11/2004 | Fowler | |
| 2004/0267572 A1 | 12/2004 | Emery et al. | |
| 2005/0043827 A1 | 2/2005 | Schaeffer et al. | |
| 2005/0165285 A1 | 7/2005 | Iliff | |
| 2005/0209891 A1 | 9/2005 | Jacobus et al. | |
| 2005/0251423 A1 | 11/2005 | Bellam et al. | |
| 2006/0004588 A1 | 1/2006 | Ananda | |
| 2006/0074713 A1 | 4/2006 | Conry et al. | |
| 2006/0080137 A1 | 4/2006 | Chambers et al. | |
| 2006/0106646 A1 | 5/2006 | Squilla | |
| 2006/0173712 A1 | 8/2006 | Joubert | |
| 2007/0040017 A1 | 2/2007 | Kozlay | |
| 2007/0061169 A1 | 3/2007 | Lorsch | |
| 2007/0061170 A1 | 3/2007 | Lorsch | |
| 2007/0185740 A1 | 8/2007 | Hooglander | |
| 2008/0027752 A1 | 1/2008 | Phan et al. | |
| 2008/0041940 A1 | 2/2008 | Weeks | |
| 2008/0223925 A1 | 9/2008 | Saito | |
| 2009/0055894 A1 | 2/2009 | Lorsch | |
| 2009/0055924 A1 | 2/2009 | Trotter | |
| 2009/0076849 A1 | 3/2009 | Diller | |
| 2009/0095810 A1 | 4/2009 | Cannon | |
| 2009/0108063 A1 | 4/2009 | Jain | |
| 2009/0133111 A1 | 5/2009 | Evans | |
| 2009/0143104 A1 | 6/2009 | Loh | |
| 2009/0240527 A1 | 9/2009 | Bluth | |
| 2009/0266882 A1 | 10/2009 | Sajkowsky | |
| 2009/0289107 A1 | 11/2009 | Prentice | |
| 2010/0042846 A1 | 2/2010 | Trotter | |
| 2010/0169123 A1 | 7/2010 | Maus | |
| 2010/0174914 A1 | 7/2010 | Shafir | |
| 2010/0181380 A1 | 7/2010 | Trotter | |
| 2010/0241519 A1 | 9/2010 | Lindahl | |
| 2010/0241520 A1 | 9/2010 | Lindahl | |
| 2010/0241521 A1 | 9/2010 | Lindahl | |
| 2010/0260388 A1 | 10/2010 | Garrett | |

OTHER PUBLICATIONS

International Preliminary Report on Patentability mailed Aug. 2, 2012 in PCT/CA2011/000075.

* cited by examiner

NETWORK AND METHOD FOR DATA INPUT, STORAGE AND RETRIEVAL

This application claims foreign priority to Canadian Patent Application No. 2,690,784, filed 22 Jan. 2010, the complete disclosure of which is incorporated herein by reference.

FIELD OF THE INVENTION

This invention relates to apparatus and methods for the exchange of data within a network and between networks, particularly data relating to (i) medical, particularly insurance information, drug information and medical records; (ii) educational, particularly between students and educators; and (iii) identification of members of a population.

BACKGROUND OF THE INVENTION

Medical records systems are mostly two-part systems, where binary information and data files (Network 1) are on separate networks. In technologically advanced areas, most of the medical data files are stored in individual locations where the data file was created. More advanced systems are able to store the data files in a central database. Individuals for whom the data files are created, herein defined as "clients", may have identification cards, using either magstrip or smartcard technology. This helps the system keep track of the client's movement and location, but does not assist or partake in the aforesaid Network 1 data file system. This results in a second and parallel Network 2 responsive to client movement for the system.

The healthcare industry is seeing a steady and increasing dependence on information technology that is rapidly transforming the practice of medicine and the delivery of care. Technology is an ever-changing and evolving aspect of modern business. In healthcare, most agree that the use of technology is essential to achieving many of the milestones critical to healthcare reform. The main reasons the industry is pushing towards these goals are the need to lower costs, the need to improve patient outcomes, the need to meet increasing privacy, security and identity concerns.

Smart cards are currently used worldwide and have grown in number significantly over the last few years. Current smart card programs focus on patient identification rather than patient records. Smart cards are portable, secure, and can be leveraged to create closer patient alignments, generate higher patient satisfaction levels, and increase revenue for the healthcare issuer.

However, a major drawback of the smartcard is that it is only able to hold relatively very small amounts of data, such as, a few lines of text to a few sheets of paper. Other larger storage device has the problem of bulky and when the size is reduced, it experienced problem of sturdiness of the device. In addition, many of the device are easily being infected by malicious software that spread from computer to computer.

Thus, there is a need for a more efficacious, convenient data input, immediate data pop-up, structurally reinforced, self-recoiling, biometrically secured, self protecting, storage and retrieval system of particular use to the medical, insurance and educational fields.

SUMMARY OF THE INVENTION

This invention, in one aspect, provides a smartcard having a chip that is able to hold sufficiently large amounts of memory, e.g. 64 GB that provides enhanced features to the functionality of the smartcard. While any large memory requires electricity to function, the use of USB technology allows this to happen.

Thus, providing a client with a device that is able to carry electronic files allows for the combination of the two aforesaid networks into one unified system. Such a device herein termed a "personal electronic carrier device" (PECD), has a built-in memory that contains software that is able to communicate within a data file network. Preferably, the PECD is of a portable credit/debit card size with a built in sufficient memory of variable sizes. Preferably, the PECD contains biometric identification that is used to identify a client. Each client carries their own PECD and uses it each time they interact for the transmission of information within the system, according to the invention. Having a group of PECDs added to a network allows of the addition of a bottom-up data storage to the traditional top-down data storage. The combination of the two storage modes creates a 'diamond-shaped' storage network. Use of such a diamond-shaped storage network, in the practise of the invention, increases the overall function, efficiency and speed of the system. Such a system clearly provides a very high level of convenience for the parties involved.

This system also enables the internetworking of client electronic files between networks, which allows the client to choose the best services offered among networks; use services in to locations beyond the geographic coverage of his chosen network; and take electronic files from one network to another.

Accordingly, in one aspect, the invention provides a personal electronic carrier device (PECD) comprising
 means for receiving PECD data;
 means for storing PECD data;
 means for transmitting PECD data directly or indirectly; and
 operating software means to effect said receiving, storing and transmitting said PECD data.

In one preferred embodiment the invention provides a personal electronic carrier device (PECD) comprising
 means for receiving PECD data;
 means for storing PECD data;
 means for transmitting PECD data directly or indirectly;
 means of storing biometric information;
 means of verifying biometric information;
 means of powering any biometric identification device;
 operating software means to effect said displaying, receiving, storing and transmitting said PECD data and;
 embedded software or hardware to protect the PECD from malicious software.

Preferably, a PECD as hereinabove defined has a storage memory of at least 1 MB, more preferably at least 4 GB, and still more preferably 8 GB.

Preferably, the PECD data is received and transmitted wirelessly.

Preferably, the PECD contain a reinforcing means, particularly pin means to enhance the structural integrity and the usability of the on-board chip.

More preferably, the PECD as hereinabove defined has the ability to recoil the chip to its original position preferably by resiliently flexible, spring and rubber-like means;

Further, preferably, biometric data is verified with an identification device on board of the PECD.

In a further aspect, the invention provides, a data network for receiving, storing and transmitting client data comprising
 (a) a PECD as hereinabove defined; and
 (b) at least one receiving, storing and transmitting data station comprising a first data station body having means for receiving station data from the group consisting of said PECD, a main database, a client, and a second or more data stations;

means for storing said station data;

means for transmitting station data; and operating software means to effect said receiving, storing and transmitting said station data in direct or indirect communication with said PECD.

In yet a further aspect, the invention provides, a data network for receiving, storing and transmitting client data comprising (a) a PECD as hereinabove defined; and (b) at least one receiving, storing and transmitting data station comprising means for receiving station data;

means for storing station data;

means for transmitting station data;

means for storing biometric data;

operating software means to effect said displaying, receiving, storing and transmitting said station data in direct or indirect communication with said PECD; and embedded software or hardware to protect the PECD from malicious software.

Preferably, a data network as hereinabove defined comprises a plurality of said data stations.

Preferably, the data station comprises means for creating a new data file for said client.

In yet a further aspect, the invention provides, data internetwork for receiving, storing and transmitting client data comprising (a) a PECD as hereinabove defined; and (b) at least one receiving, storing and transmitting data station comprising means for receiving station data between two networks;

means for storing station data between two networks;

means for transmitting station data between two networks;

means for storing biometric data between two networks;

operating software means to effect said displaying, receiving, storing and transmitting said station data in direct or indirect communication with said PECD; and embedded software or hardware to protect the PECD from malicious software.

Preferably, between two data networks as hereinabove defined comprises a plurality of said data stations.

Preferably, the data station in any network comprises means for creating a new data file for said client.

In a yet further aspect, the invention provides a data network as hereinabove defined further comprising a main data database comprising means for receiving main data from the group consisting of said PECD, a main database, a client, and a second or more data stations;

means for storing main data;

means for transmitting main data;

operating software means to operably effect directly or indirectly said receiving, storing and transmitting said main data to and from said PECD and said data station; and wherein said data station and said PECD are in direct or indirect communication with said main database.

In a still yet further aspect, the invention provides a data network as hereinabove defined further comprising a main data database comprising means for receiving main data;

means for storing main data;

means for transmitting main data;

means for storing biometric data;

operating software means to operably effect directly or indirectly said receiving, storing, displaying and transmitting said main data to and from said PECD and said data station; and wherein said data station and said PECD are in direct or indirect communication with said main database.

Preferably, the data station comprises means for transmitting said new data file to said PECD and said main database.

The main data herein comprises station data and client data.

In a still yet further aspect, the invention provides a method for receiving, storing and transmitting client data in at least one data station and a personal electronic carrier device (PECD) of a network, said method comprising feeding client data into said data station;

storing said client data in said data station;

transmitting said client data to said PECD; and storing said client data in said PECD.

In a still yet further aspect, the invention provides a method for receiving, storing displaying and transmitting client data in at least one data station and a personal electronic carrier device (PECD) of a network, said method comprising feeding client data into said data station;

storing said client data in said data station;

transmitting said client data to said PECD; and storing said client data in said PECD.

More preferably, the method further comprises storing said client biometric data in said PECD.

Preferably, the method, as hereinabove defined, comprises feeding and storing said client data to a main database of said network.

More preferably, the method, as hereinabove defined, comprises retrieving and transmitting stored client data to at least one of said data stations and said PECD.

Preferably, the method, as hereinabove defined, comprises feeding client data into a plurality of data stations; and comprises feeding client data into said data station;

storing said client data in said data station;

transmitting said client data to said PECD;

storing said client data in said PECD; and storing said client biometric data in said PECD.

In some cases, the locations or stations can access data files from the main database. However, there are situations when this method will be hindered, e.g. when some data files are very large. It may be more convenient to access the data from a PECD available on site. Another advantage of the PECD is that the data can be accessed outside of the main network.

It can be seen that although the main database is the heart of the entire network, each station or location can create new data files for clients. Preferably, the data files are stored at the location of creation, and then a copy of the data files are backed up to the main database. The data files are copied again and then, or subsequently, stored on a PECD if it is, or not, available at the time of transfer. Once the data file is in the main database, other locations are able to retrieve the data files for download/viewing. Outside of the aforesaid internal network locations, the main database files could be accessed by kiosk terminals. The PECD can be connected to a kiosk terminal to retrieve any data files that were not available at the time it was present at one of the locations.

It can be seen that the networks components are variable, in that, the networks can function with missing components, and, which, in some situations it is preferable to omit. For example, a system with a single location or station will not need the main database, or a kiosk, and none of the other locations. This simplified data flow network, thus, creates a top-down storage system from the location to the PECD, and a bottom-up storage from the PECD to the location. Any combination of the components is possible, as long as there is a PECD to provide the bottom-up storage method and a receiving station or main database.

Data file transfers are, preferably, bidirectional, wherein any component has the ability to send, store and receive data files within the system network. However, in some situations it may be beneficial to block one of the directions for the overall benefit of the system.

In a further embodiment, a further data flow arrangement is a system where a PECD acts as a center piece in communication with a plurality of locations, stations or between networks. The type of location will vary depending on the specific network. For example, in the medical field, location type A could be a pharmacy; while location type B a doctor's office or a diagnostic clinic. In a further example, in the medical field, location A could be a clinic using central database M; while location B is a hospital using central database N.

In a further embodiment, a PECD as hereinabove defined comprising a planar body having a portion defining an aperture and a memory chip comprising
  means for receiving PECD data;
  means for storing PECD data;
  means for transmitting PECD data directly or indirectly; and
  operating software means to effect said receiving, storing and transmitting said PECD data; said memory chip retained within said aperture in coplanar alignment with said planar body.

In a further embodiment, a PECD as hereinabove defined wherein said memory chip further comprises
  means of storing biometric information;
  means of verifying biometric information;
  means of powering a biometric identification device;
  operating software means to effect said displaying, receiving, storing and transmitting said PECD data and;
  embedded software or hardware to protect the PECD from malicious software.

In a further embodiment, a PECD is as hereinabove defined wherein said memory chip is rotatably retained within said aperture.

In a further embodiment a PECD as hereinabove defined comprising an elongate memory chip retaining member located within said planar body and said memory chip.

In a further embodiment a PECD as hereinabove defined is wherein said retaining member is formed of a metal, a plastics material or carbon fiber.

In a further embodiment a PECD is as hereinabove defined comprising a resiliently flexible member located within said planar body and said memory chip whereby after displacement of said memory chip out of coplanar alignment with said planar body under the action of a displacing force, said resiliently flexible member effects return of said memory chip to said coplanar alignment when said displacing force is removed.

In a further embodiment a PECD as hereinabove defined is wherein said resiliently flexible member is in the form of an elongate member selected from a thread, line, fiber and the like and formed of rubber, carbon fibre, or a plastics material.

By elongate in this specification is meant the retaining member is of sufficient length to retain said member within said body and memory chip.

In a further embodiment a PECD as hereinabove defined is wherein said planar body has a thickness of less than 2.5 mm In preferred embodiments, the PECD according to the invention is provided with a biometric information reading means containing data, such as, for example, fingerprint, retina and/or DNA data of a user—patient of use in an emergency. Such a user may be unconscious and not able to provide a password. Aforesaid biometric access provides the ability to authenticate the patient and allow access of the stored data.

In further preferred embodiments, the PECD is provided with automatic protection software to prevent the unwanted access to and corruption of files in an emergency.

BRIEF DESCRIPTION OF THE DRAWINGS

In order that the invention may be better understood, preferred embodiments will now be described, by way of example only, wherein.

DETAILED DESCRIPTION OF PREFERRED EMBODIMENTS

Figure 1:
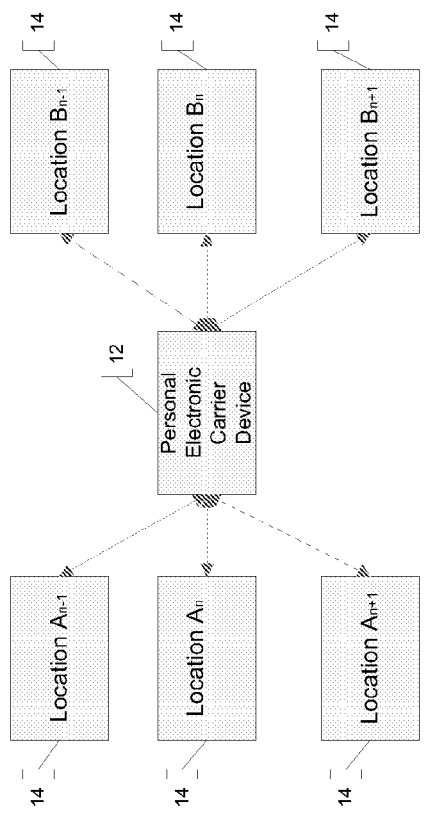
FIG. 1 is a data network having a portable electronic carry device (PECD) in communication with a plurality of data stations/locations, according to the invention.

FIG. 1 shows generally as 10, a network having a PECD 12 in communication with a plurality of locations or data stations 14—six in the embodiment shown. Locations A, e.g. pharmacies or diagnostic clinics are able to transmit medical information to the PECD. The PECD is then able to bring information, preferably, portably, to a desired location B, e.g. health care facilities, and the like, for the facility to receive updated data. Each of locations A and B are, thus, connected via the network created by the PECD.

Figure 2:
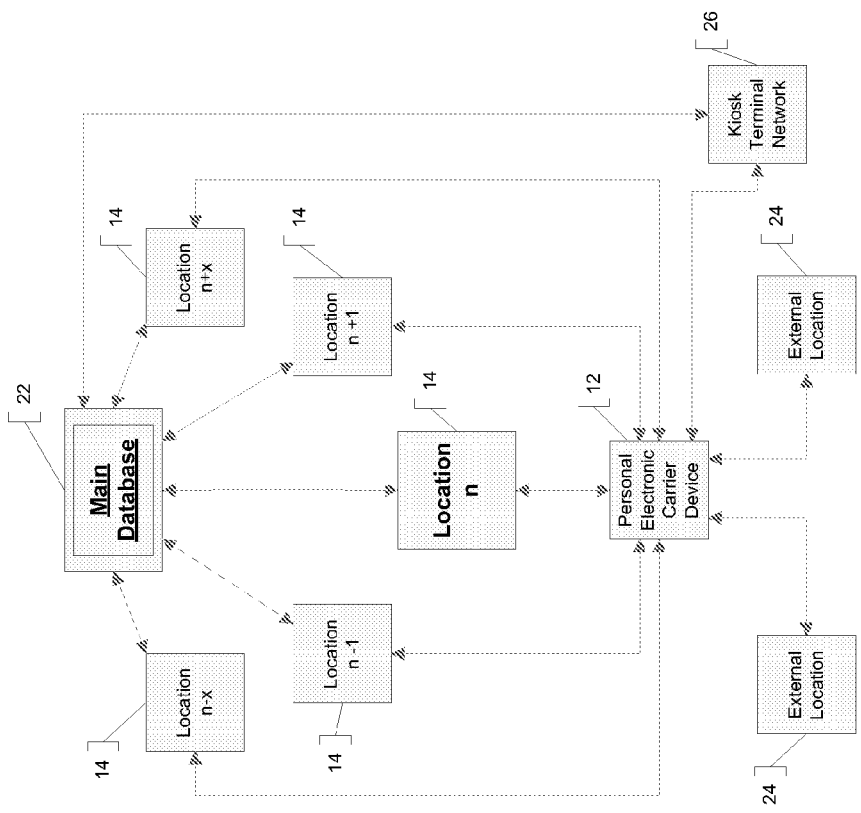
FIG. 2 is a further data network having a PECD, plurality of data stations and a main database, according to the invention.
Figure 2A:
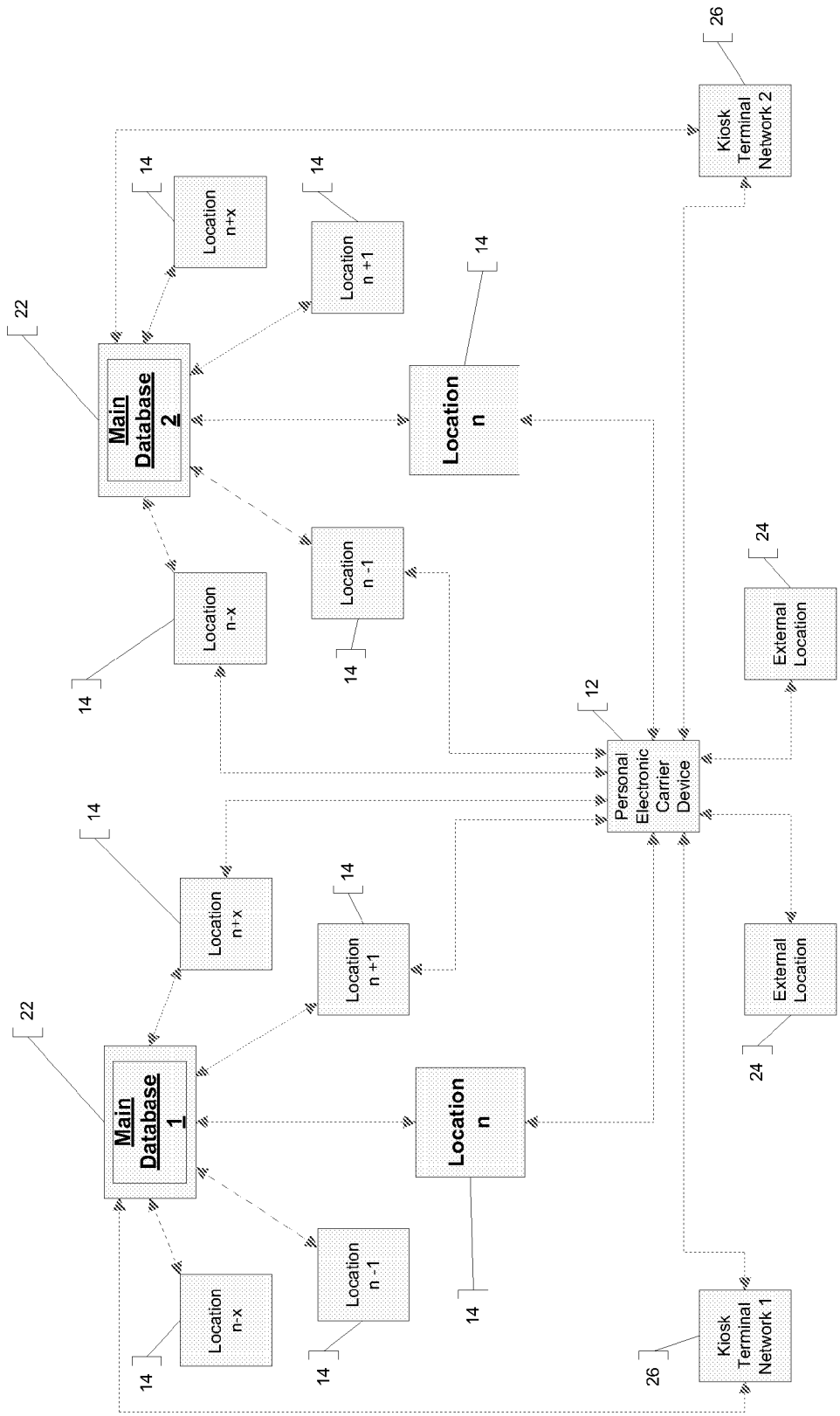
FIG. 2a is a internetwork having two networks and a PECD, plurality of data stations and two main databases, according to the invention.

FIG. 2 and FIG. 2a show generally as 20, a network and networks having a PECD 12, plurality of data stations/locations 14 and main database 22.

Network 20 defines a top-down, and bottom-up data receiving, transfer and storage system. Although information can travel bidirectionally, it is, however, often preferred in some locations to be unidirectional. Preferably, there is main database 22 that can directly and indirectly reach all the components in the system. In the absence of main database 22, individual locations 14 perform the role of main database 22. Locations 14 may have a minimum of one, and an unlimited maximum. PECD 12 may be considered to be an end user.

PECD 12 can undergo a bidirectional data exchange within networks 10 and 20. The data will be unique to the individual person(s) in possession of PECD 12. Data from PECD 12 can be sent and received from an external party 24 that is not a part of the network, if desired. PECD 12 can undergo data transfer directly with main database 22 via a kiosk terminal 26, if desired.

Figure 3A:
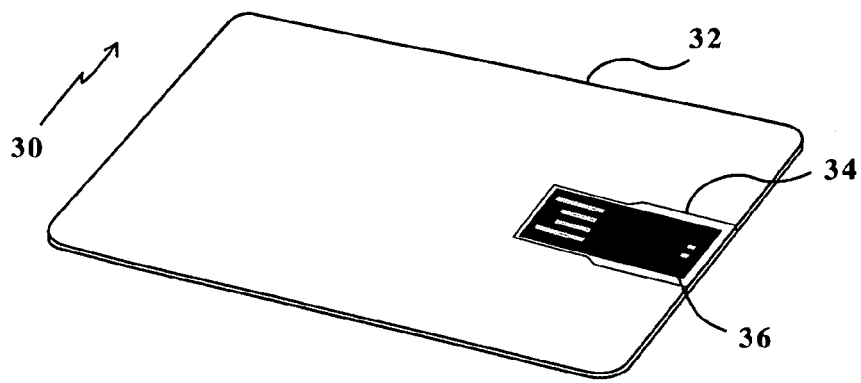
FIGS. 3a and 3b are perspective views of a PECD, according to the invention.
Figure 3B:
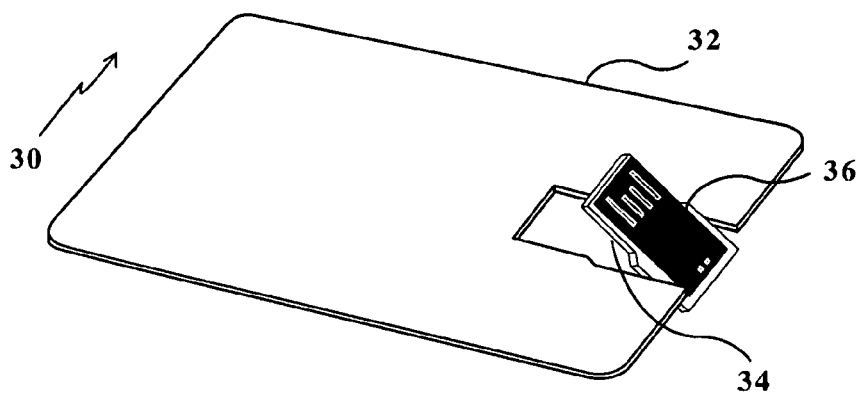
Figure 4:
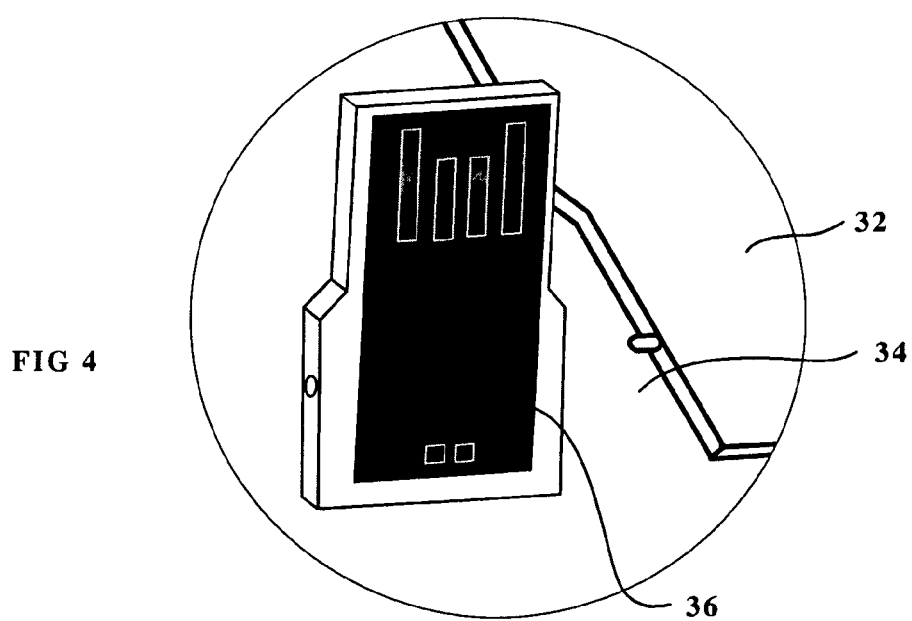
FIG. 4 is a perspective view of a memory chip of use in the practise of the invention.

FIGS. 3a and 3b show generally as 30 a credit card-sized shaped planar member of less than 2 mm thick and having a plastics, carbon fiber or titanium body 32 having a portion defining an aperture 34 retaining a 8 GB member chip 36. Chip 36 is swivable within aperture 34 and removable therefrom (FIG. 4). Memory chip 36 may be substituted and interchanged predicated on the utility and application required. Chip 36 can be detached from body 32 for the convenience of reaching difficult locations of USB ports.

Figure 5:
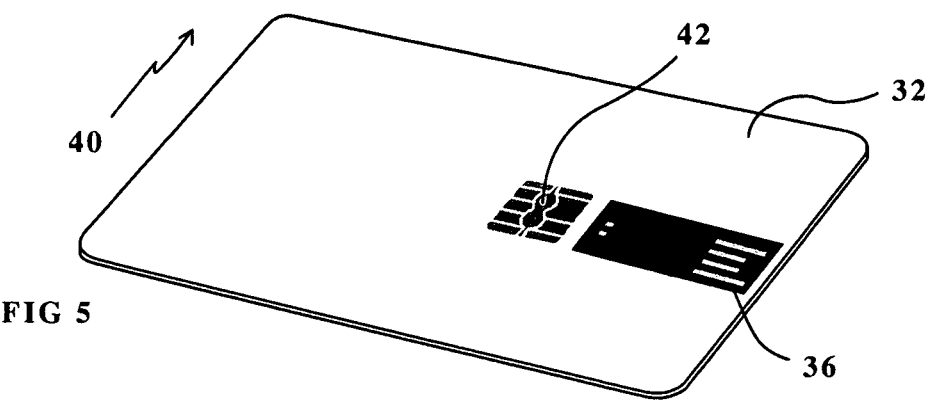
FIG. 5 is a perspective view of a PECD storing USB chip technology combined with smart chip technology, according to the invention.

FIG. 5 shows card 40 having memory chip 36 combined with smart card chip 42.

Figure 6:
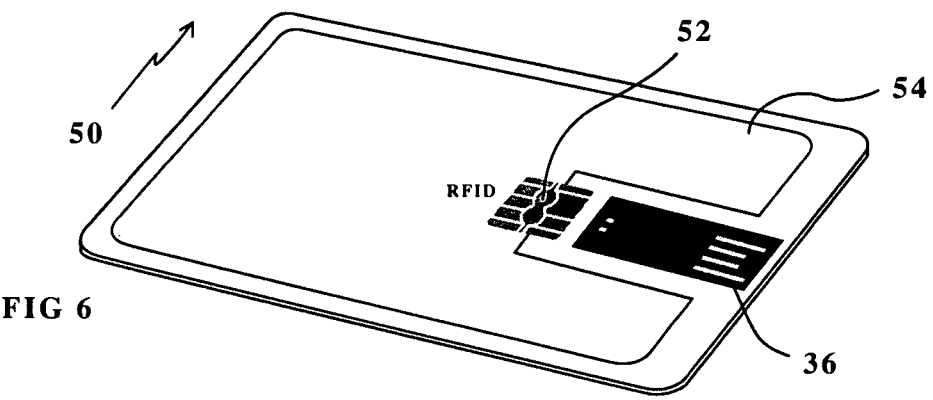
FIG. 6 is a perspective view of a PECD storing USB chip technology combined with contactless smart chip RFID technology.

FIG. 6 shows PECD 50 having USB chip 36 and RFID contactless smart chip 52 within card 54, antenna 56 within chip.

Figure 7:
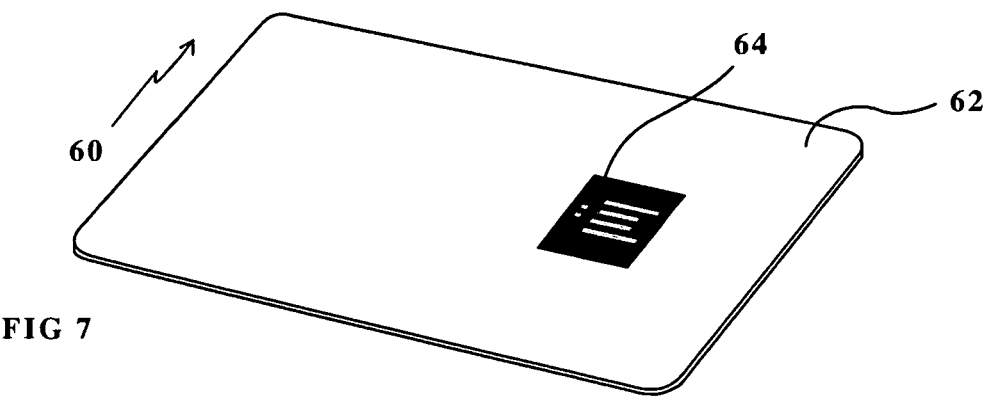
FIG. 7 is a perspective view of an alternative PECD having small, thin and narrow dimensions than the embodiment shown in FIG. 3, according to the invention.

FIG. 7 shows a PECD 60 designed to minimize the dimensions, particularly the thickness of card 62 bearing USB 64.

Figure 8:
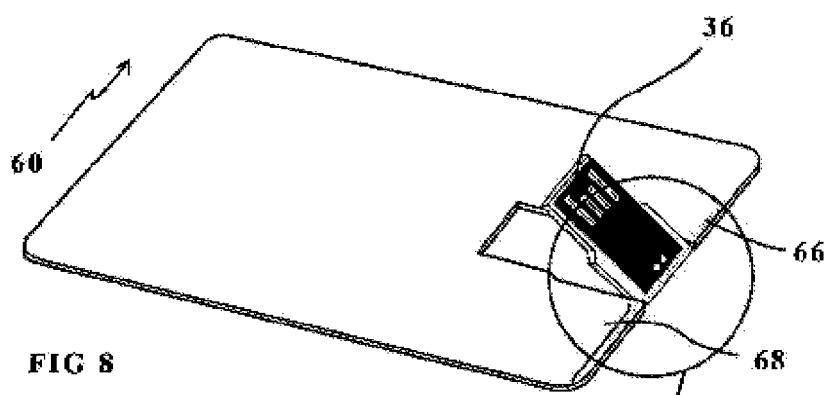
FIG. 8 is a perspective view of a PECD having a reinforcing member according to the invention.
Figure 8A:
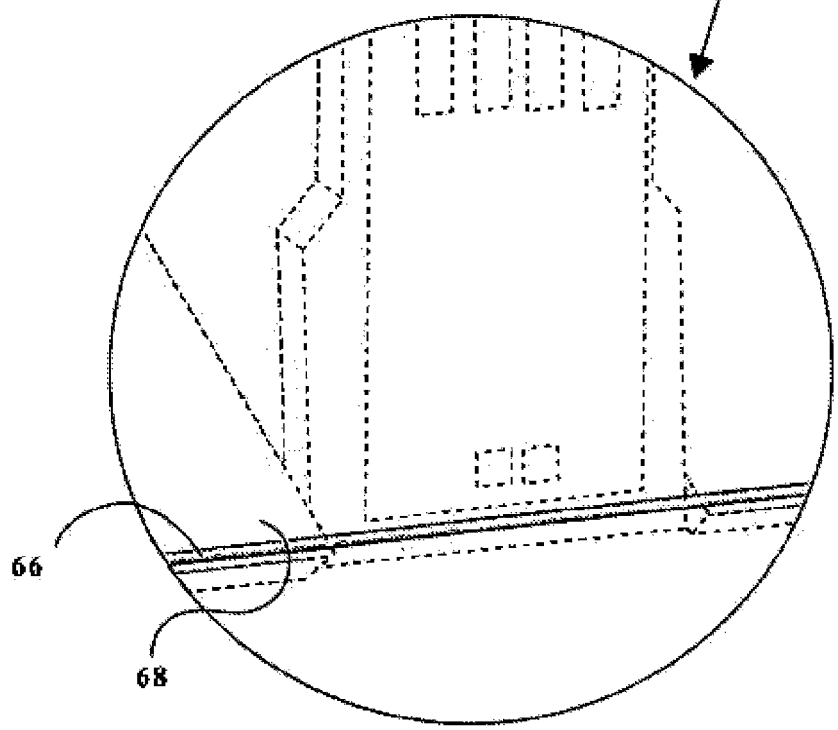
FIG. 8A is an enlarged part section of the PECD of FIG. 8.

FIG. 8 shows a PECD 60 having a reinforcing longitudinal steel needle 66 partially or completely across the width of PECD 60 at the lower end 68 and through chip 36 within PECD 60 rotatably retains chip 36 within PECD 60. Alternative suitable reinforcing materials, such as, for example, formed of a plastics material, metal or carbon fibre may be used.

We have found that the presence of reinforcing needle 66 in a desirable, relatively thin PECD 60 prevents chip 36 from being dislodged when the PECD is bent or twisted. In the absence of the retaining needle, rod, or the like, a small amount of torque causes thin cards to dislodge chip 36A. PECD thickness of less than 2 mm e.g. as thin as a typical USB stick is preferred for physical connection to a computer.

Figure 9:
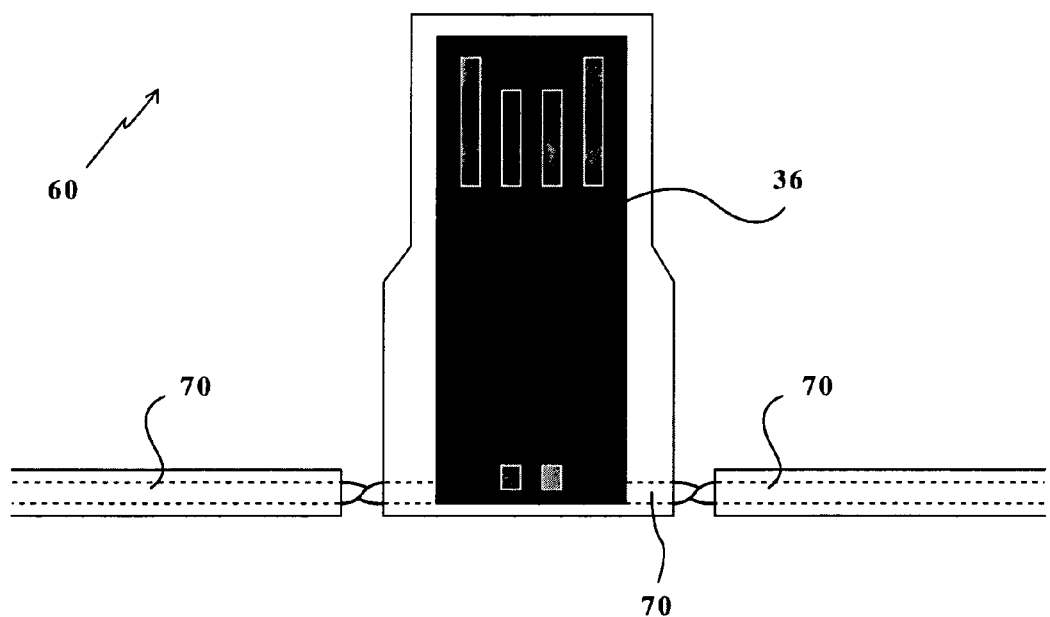
FIG. 9 is an end vertical view, in part, of a PECD with an upstanding chip and resiliently flexible thread under tension, according to the invention; and wherein the same numerals denote like parts.

Reference to FIG. 9 shows use of an elongate rubber thread 70 extending through lower end 68 of PECD 60 and chip 36 at terminal portion 72. When chip 36 and PECD are coplanar, thread 70 is in its relaxed state. When chip 36 is pulled out of alignment for insertion, thread 70 is under torsion. Release of chip 36 allows of relaxation of thread 70 and recoil of chip 36 back into coplanarity with PECD 60. Alternatively, other resiliently flexible materials such as, for example, suitable plastics material, carbon fiber, metallic coil springs, and the like may be used. These materials are preferably retained within the PECD 60 and chip 36 by a suitable adhesive.

The PECD and networks as hereinabove described have particular utility in the transfer of medical data, including, but not limited to, insurance information, prescription drug information, and medical records. However, the system can also function as an educational distribution web to provide information from educators to students and vice versa. The system can also function as an identification/data retention system to retain information including biometric information on members of a population.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The invention claimed is:

1. A personal electronic carrier device (PECD) comprising
   (a) a planar body having a portion defining an aperture and a memory chip, said memory chip comprising (i) means for receiving PECD data; (ii) means for storing PECD data; (iii) means for transmitting PECD data directly or indirectly; and (iv) operating software means to effect said receiving, storing and transmitting said PECD data wherein said memory chip is rotatably retained within said aperture in coplanar alignment with said planar body; and
   (b) a resiliently flexible member located within said planar body and said memory chip whereby after displacement of said memory chip out of coplanar alignment with said planar body under the action of a displacing force, said resiliently flexible member effects return of said memory chip to said coplanar alignment when said displacing force is removed.

2. A PECD as claimed in claim 1 having a storage memory of at least 1 MB.

3. A PECD as claimed in claim 1 having a storage memory of at least 8 GB.

4. A PECD as claimed in claim 1 wherein said PECD data is received and transmitted wirelessly.

5. A PECD as claimed in claim 1 wherein said memory chip further comprises:
   means of storing biometric information;
   means of verifying biometric information;
   means of powering a biometric identification device [operating software means to effect said receiving, storing and transmitting said PECD data]; and
   embedded software or hardware to protect the PECD from malicious software.

6. A PECD as claimed in claim 5 comprising an elongate memory chip retaining member located within said planar body and said memory chip.

7. A PECD as claimed in claim 6 wherein said retaining member is formed of a metal, a plastics material or carbon fiber.

8. A PECD as claimed in claim 7 wherein said resiliently flexible member is in the form of an elongate member selected from a group consisting of thread, line and fiber, the elongate member formed of rubber, carbon fibre, or a plastics material.

9. A PECD as claimed in claim 8 wherein said planar body has a thickness of less than 2.5 mm.

10. A PECD as claimed in claim 1 wherein said PECD data is selected from the group consisting of medical, educational, personal identification data and financial data.

11. A data network for receiving, storing and transmitting client data comprising
    (a) a personal electronic carrier device (PECD) comprising;
       means for receiving PECD data;
       means for storing PECD data;
       means for transmitting PECD data directly or indirectly; and
       operating software means to effect said receiving, storing and transmitting said PECD data; and
    (b) at least one receiving, storing and transmitting data station comprising;
       a first data station body having means for receiving station data from the group consisting of said PECD, a main database, a client, and at least a second data station;
       means for storing said station data;
       means for transmitting station data; and operating software means to effect said receiving, storing and transmitting said station data in direct or indirect communication with said PECD.

12. A data network as claimed in claim 11 further comprising means for storing biometric data;

operating software means to effect said displaying, receiving, storing and transmitting said station data in direct or indirect communication with said PECD; and embedded software or hardware to protect the PECD from malicious software.

13. A data network as claimed in claim 11 comprising a plurality of said data stations.

14. A data network as claimed in claim 11 further comprising a main data database comprising means for receiving main data from the group consisting of said PECD, a main database, a client, and a second or more data stations;

means for storing main data;

means for transmitting main data;

operating software means to operably effect directly or indirectly said receiving, storing and transmitting said main data to and from said PECD and said data station; and wherein said data station is in direct or indirect communication with said main database.

15. A network as claimed in claim 11 wherein said data station comprises means for creating a new data file for said client.

16. A network as claimed in claim 15 wherein said data station comprises means for transmitting said new data file to said PECD, one or more other data stations and said main database.

17. A internetwork as claimed in claim 11 wherein said data station comprises means for transmitting said new data file to said PECD, one or more other data stations and said main databases.

18. A network as claimed in claim 11 wherein said PECD data, client data and main data is selected from the group consisting of medical, educational, identification and financial data.

* * * * *